United States Patent [19]

Sunagawa et al.

[11] Patent Number: 5,113,020
[45] Date of Patent: May 12, 1992

[54] PROCESS FOR PRODUCING P-HALOGENOBENZOPHENONE DERIVATIVES

[75] Inventors: Kazuhiko Sunagawa; Nobuyuki Kusano, both of Iwaki, Japan

[73] Assignee: Kureha Kagaku Kogyo K.K., Tokyo, Japan

[21] Appl. No.: 751,000

[22] Filed: Aug. 28, 1991

[30] Foreign Application Priority Data

Sep. 6, 1990 [JP] Japan .................. 2-234347
Apr. 12, 1991 [JP] Japan .................. 3-106486

[51] Int. Cl.⁵ .............................. C07C 45/43
[52] U.S. Cl. .................. 568/323; 570/199; 570/191
[58] Field of Search ........ 570/199, 191, 194; 568/323

[56] References Cited

U.S. PATENT DOCUMENTS

| | | | |
|---|---|---|---|
| 4,414,406 | 11/1983 | Fields | 568/323 |
| 4,453,012 | 6/1984 | Desbois | 568/323 |
| 4,454,350 | 6/1984 | Desbois | 568/323 |
| 4,978,798 | 12/1990 | Stults | 568/323 |

FOREIGN PATENT DOCUMENTS

| | | | |
|---|---|---|---|
| 147299 | 7/1985 | European Pat. Off. | 568/323 |
| 2534906 | 4/1984 | France | 568/323 |
| 61-221146 | 1/1986 | Japan | 568/323 |
| 2-121945 | 5/1990 | Japan | 568/323 |

*Primary Examiner*—James H. Reamer
*Attorney, Agent, or Firm*—Lowe, Price, LeBlanc & Becker

[57] ABSTRACT

The present invention provides a process for producing a p-halogenobenzophenone derivative of a high purity in a high yield at a low cost in the presence of a repeatedly usable catalyst having a long life and free from the problem of waste water treatment without using any chemical of a strong toxicity. According to the present invention, the p-halogenobenzophenone derivative is produced by reacting an (un)substituted benzotrichloride of the following formula (I) with a halogenobezene of the following formula (II) in the presence of a catalyst selected from the group consisting of alumina, nickel sulfate, zirconium oxide, amorphous silica/alumina and a mixture of two or more of them or a catalyst obtained by treating these compounds with an acid and hydrolyzing the resulting bisphenyldichloromethane of the following formula (III):

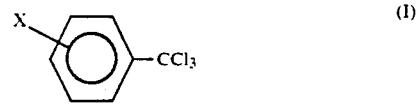

(I)

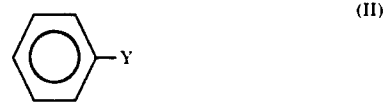

(II)

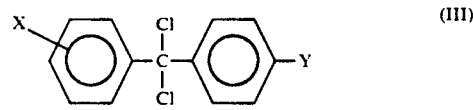

(III)

wherein X represents a halogen atom or a hydrogen atom and Y represents a halogen atom.

3 Claims, No Drawings

PROCESS FOR PRODUCING P-HALOGENOBENZOPHENONE DERIVATIVES

BACKGROUND OF THE INVENTION

1. Field of the Invention

The present invention relates to a process for producing a p-halogenobenzophenone derivative useful as a monomer for heat-resistant polymers.

2. Description of the Related Arts p-Halogenobenzophenone derivatives are recently especially noted as monomers for heat-resistant polymers such as polyether ketones and polythioether ketones and a development of a process for producing them at a low cost is eagerly demanded. Known processes for producing halogenobenzophenone derivatives include those wherein a halogenobenzene is directly acylated, such as (1) a process wherein chlorobenzoyl chloride is reacted with a halogenobenzene, (2) a process wherein a halogenobenzene is reacted with phosgene (see European Patent No. 147,299), and (3) a process wherein chlorobenzene is reacted with carbon monoxide (see Japanese Patent Laid-Open No. 221146/1986), as well as a process wherein a 1,1-dichloro-2,2-bis(halogenopheny)ethylene is oxidized with nitric acid, a process wherein p-chlorobenzotrichloride is reacted with chlorobenzene in the presence of a Lewis acid catalyst such as iron chloride or aluminum chloride (see French Patent No. 2,534,906) and a process wherein the reaction is conducted in the presence of a crystalline aluminosilicate (see Japanese Patent Laid-Open No. 121945/1990).

However, the above-described prior art processes have problems. Namely, the process wherein a halogenobenzene is directly acylated with phosgene or carbon monoxide is unfavorable to be conducted on an industrial scale, since phosgene and carbon monoxide are chemicals having a strong toxicity. The process wherein a 1,1-dichloro-2,2-bis(halogenophenyl)ethylene is oxidized with nitric acid has a problem in the production per se of the starting material, since the production of the starting material causes environmental pollution. Further the process wherein chlorobenzene is directly acylated with an acid chloride in the presence of a Lewis acid and the process wherein p-chlorobenzotrichloride is reacted with chlorobenzene in the presence of a Lewis acid catalyst such as iron chloride or aluminum chloride have a problem of catalyst removal and a problem of waste water treatment. Namely, when a Lewis acid catalyst soluble in the reaction system, such as iron chloride or aluminum chloride, is used, the whole reaction liquid must be washed with an acid and water after the completion of the reaction so that the catalyst migrates into the aqueous layer. This necessitates a complicated operation and, in addition, water used in a large quantity for washing posed a problem of environmental pollution if it is discharged as it is.

Although the process wherein p-chlorobenzotrichloride is reacted with chlorobenzene in the presence of crystalline aluminosilicate (zeolite) is a preferred process free from the above-described problems, it is yet unsatisfactory for conducting on an industrial scale, since the life of the catalyst is short and a complicated catalyst regeneration is necessary for the repeated use. In particular, the recovery of the activity thereof is slight when it is washed with a solvent and the conversion is sharply reduced when this catalyst is repeatedly used after mere washing with the solvent. Thus when zeolite is repeatedly used as the catalyst, a problem is posed that it must be frequently regenerated by heat treatment or the like.

Thus all the prior art processes involve problems when they are conducted on an industrial scale.

SUMMARY OF THE INVENTION

Therefore, the present invention aims at solving the above-described problems of the prior art processes. Namely, an object of the present invention is to provide a process for producing a p-halogenobenzophenone derivative of a high purity in a high yield at a low cost in the presence of a repeatedly usable catalyst having a long life and free from the problem of waste water treatment without using any chemical of a strong toxicity.

The inventors have completed the present invention after intensive investigations made for the purpose of finding a catalyst having a sufficiently long catalytic life and being repeatedly usable many times without being regenerated and also reusable by regeneration when used in place of the crystalline aluminosilicate as the catalyst for the above-described prior art process which comprises reacting p-chlorobenzotrichloride with chlorobenzene and in which no strongly toxic chemical is used and no problem of environmental pollution will occur, thus being relatively less problematic among other processes.

The constructive feature of the present invention resides in that an (un)substituted benzotrichloride of the following formula (I) is reacted with a halogenobenzene of the following formula (II) in the presence of a catalyst selected from the group consisting of alumina, nickel sulfate, zirconium oxide, amorphous silica/alumina and a mixture of two or more of them or a catalyst obtained by treating these compounds with an acid and the resulting bisphenyldichloromethane of the following formula (III) is hydrolyzed to give a p-halogenobenzophenone:

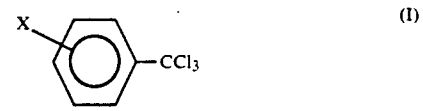

(I)

(II)

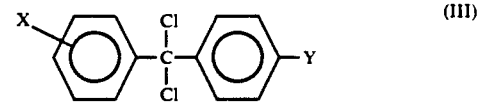

(III)

wherein X represents a halogen atom or a hydrogen atom and Y represents a halogen atom.

The p-halogenobenzophenone derivatives produced by the present invention are benzophenone of the following formula having a halogen atom at the p-position of at least one benzene ring of the benzophenone:

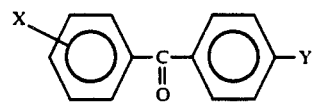

wherein X represents a halogen atom or a hydrogen atom and Y represents a halogen atom.

The term "amorphous silica/alumina" as used herein refers to an aluminum silicate having no X-ray diffraction pattern, such as silica/alumina obtained in the form of a hydrogel by the reaction of an aqueous silicate solution with an aqueous aluminum salt solution.

DETAILED DESCRIPTION OF PREFERRED EMBODIMENTS

Now the detailed description will be made on the present invention.

The benzotrichloride of the formula (I) which is one of the starting materials to be reacted is a benzotrichloride in which the benzene ring is unsubstituted or substituted with a halogen atom such as a chlorine, fluorine, bromine or iodine atom. A benzotrichloride having a halogen atom at the p-position is preferably used.

In conducting the process of the present invention, the molar ratio of the starting benzotrichloride of the formula (I) to the halogenobenzene of the formula (II) ranges from 1:0.2 to 1:15. Usually a less expensive starting compound is used in excess. When a reaction solvent is used, the molar ratio ranges from 1:1 to 1:2, preferably from 1:1.1 to 1:1.2. The reaction solvent usable herein is, for example, 1,1,2,2-tetrachloroethane.

The catalyst used in the present invention is selected from the group consisting of alumina, nickel sulfate, zirconium oxide and amorphous silica/alumina or is a solid acid catalyst obtained by treating such a catalyst with an acid. The catalyst selected from the group consisting of alumina, nickel sulfate, zirconium oxide and amorphous silica/alumina may be used either singly or in the form of a mixture of two or more of them. The catalyst may be treated with an acid by immersing it in an acid such as sulfuric or hydrofluoric acid. By the acid treatment, the conversion or selectivity toward the p-isomer is improved. The amount of the catalyst used varies depending on the kind and shape of the catalyst and the type of the reaction (batchwise or continuous process) and the scale of the reaction. Therefore, the amount of the catalyst to be used is suitably determined depending on the catalyst used and the type of the reaction. It is usually an amount sufficient for obtaining an economical reaction velocity. When the reaction is conducted batchwise on a relatively small scale, the catalyst is used in an amount ranging from 10 to 200 g, preferably from 50 to 150 g, per mole of the benzotrichloride of the formula (I).

The catalyst used in the present invention is repeatedly usable. For example, the catalyst used in conducting the reaction batchwise and then separated from the reaction mixture can be subjected to the reaction of the next batch after merely washing it with a halogenobenzene which is one of the reactants. Reductions in the conversion and yield are only slight even after repeatedly using it several tens of times. Thus as compared with zeolite with which the conversion is sharply lowered after repeated use, the catalyst used in the present invention exhibits a remarkably excellent effect.

The reaction is conducted at a temperature ranging from 80° to 200° C., preferably from 100° to 150° C. When the reaction temperature is too low, the reaction hardly proceeds, while when it exceeds 200° C., high boiling compounds are formed as by-products in a large amount unfavorably. The reaction time is 0.2 to 20 hours, desirably 0.5 to 10 hours.

When the above-described starting materials are reacted as described above according to the present invention, a reaction liquid mainly comprising a bisphenyldichloromethane of the formula (III), i.e. bis(halogenophenyl)dichloromethane or halogenophenylphenyldichloromethane and its hydrolyzate, i.e. a mono- or dihalogenobenzophenone, as the main products is obtained. After cooling, the catalyst is separated from the reaction mixture by filtration and the filtrate is distilled to recover unreacted starting materials.

By hydrolyzing the distillation residue, a mono- or dihalogenobenzophenone can be quantitatively obtained. More specifically, for example, the distillation residue remaining after an unreacted matter has been removed is dissolved in a solvent mixture of methanol and dilute hydrochloric acid, the solution is heated under reflux to conduct hydrolysis, and the reaction mixture is left to cool to form crystals. The crystals are separated by filtration to give the intended p-halogenobenzophenone derivative of a quite high purity.

The present invention basically comprises reacting a benzotrichloride with a halogenobenzene in the presence of the above-described catalyst. As for such a reaction, an example wherein a crystalline aluminosilicate, i.e. zeolite, is used as the solid acid catalyst is disclosed in the Japanese Patent Laid-Open No. 121945/1990 as described above. However, the catalyst used in the present invention is characterized in that it is repeatedly usable merely by washing it with the starting material and that it has a long catalytic life unlike zeolite. It has been quite unexpectable that the amorphous silica/alumina which is one of the catalysts usable in the present invention might have the above-described excellent effects, though its components is similar to that of zeolite.

According to the process of the present invention, the p-halogenobenzophenone derivative can be produced in a yield of 80% or more and the isolated p-halogenobenzophenone derivative has a purity of as high as at least 99%. In addition, the solid acid catalyst can be separated by mere filtration after the completion of the reaction. The separated catalyst can be repeatedly used many times after the mere washing treatment. Thus the process of the present invention is free from the problem of waste water treatment as posed when the conventional soluble Lewis acid catalyst is used or the problem of the shortness of the catalyst life as posed when zeolite is used and, therefore, it is quite suitable as the industrial production process.

EXAMPLES

The following Examples will further illustrate the present invention.

EXAMPLE 1

In a 200-ml three-necked flask provided with a stirrer, 22.9 g (0.1 mol) of p-chlorobenzotrichloride, 90 g (0.8 mol) of chlorobenzene and 10 g of silica/alumina (3 mm × 3 mm pellets of X-632HN, a product of Nikki Chemical Co., Ltd.) were placed and reacted at 124° to 125° C. for 4 hours. After the completion of the reaction, the catalyst was separated by filtration and washed with chlorobenzene for reuse. The obtained reaction liquid was analyzed by gas chromatography to find that the conversion was 52.0% and the total formation rate of bis(p-chlorophenyl)dichloromethane (A) and p,p'-dichlorobenzophenone (B) was 44.7% based on the fed p-chlorobenzotrichloride (molar ratio of A to B: 89/11). The yield was 86% based on the consumed starting materials. The ratio of the p,p'-compound to the o,p'-compound was 12.2:1.

The obtained reaction liquid was distilled under a reduced pressure (12 mmHg. 93° C. or below) to recover unreacted chlorobenzene and p-chlorobenzotrichloride. 10 ml of 1N hydrochloric acid and 90 ml of methanol were added to the residue and the mixture was refluxed for 30 minutes to hydrolyze. The hydrolysis reaction liquid was left to cool and crystals thus formed were separated by filtration and washed with a small quantity of methanol to give 10.10 g of crystalline p,p'-dichlorobenzophenone having a purity of 99.8%.

Methanol used for the washing as described above was concentrated and crystals thus formed were recrystallized from methanol/water to give 0.91 g of p,p'-dichlorobenzophenone having a purity of 98.5%. The total yield of isolation of the product was 84.2% based on the consumed p-chlorobenzotrichloride.

EXAMPLE 2

A similar reaction to that of Example 1 was repeated except that the silica/alumina catalyst was replaced by each catalyst listed in Table 1. The conversion and reaction yield of dichlorobenzophenone are given in Table 1.

TABLE 1

| Catalyst | Conversion (%) | Yield of p,p'-compound (%) | Yield of o,p'-compound (%) |
|---|---|---|---|
| nickel sulfate | 59.4 | 79.3 | 17.2 |
| pulverized silica/alumina | 61.3 | 87.1 | 6.9 |
| silica/alumina treated with sulfuric acid | 63.7 | 83.0 | 9.3 |
| silica/alumina treated with HF | 42.5 | 87.3 | 6.9 |
| alumina | 35.7 | 81.4 | 9.4 |
| zirconium oxide treated with sulfuric acid | 69.6 | 82.9 | 11.5 |

(Notes)
nickel sulfate: prepared by calcining special grade nickel sulfate hexahydrate (a product of Kanto Chemical Co., Inc.) at 350° C. for 6 hours.
pulverized silica/alumina: prepared by pulverizing X-632HN (a product of Nikki Chemical Co. Ltd.) with a mortar and sieving through a 250-mesh filter.
silica/alumina treated with sulfuric acid: prepared by immersing X-632HN (a product of Nikki Chemical Co., Ltd.) in 10% sulfuric acid for 6 hours and then calcining it at 500° C. for 3 hours.
silica/alumina treated with HF: prepared by calcining No. E58L1 (a product of Nikki Chemical Co., Ltd.), at 150° C. for 3 hours.
alumina: prepared by calcining neutral alumina for chromatography at 550° C. for 2 hours.
zirconium oxide treated with sulfuric acid: prepared by treating zirconium hydroxide with 1 N sulfuric acid calcining it at 500° C. for 3 hours.

EXAMPLE 3

The silica/alumina catalyst used in Example 1 was washed with 100 ml of chlorobenzene and subjected to the reaction under the same conditions as those of Example 1. The catalyst was repeatedly used for the reaction 20 times in the same manner as that described above. The conversion and reaction yield of p,p'-dichlorobenzophenone are given in Table 2.

TABLE 2

| Number of times of repetition | Conversion (%) | Yield (%) |
|---|---|---|
| 2 | 50.6 | 82.5 |
| 4 | 50.0 | 82.5 |
| 6 | 50.9 | 83.5 |
| 8 | 52.0 | 82.5 |
| 10 | 49.7 | 86.7 |
| 12 | 50.4 | 84.3 |
| 14 | 47.6 | 86.6 |
| 16 | 46.6 | 88.8 |
| 20 | 47.6 | 89.2 |

EXAMPLE 4

The reaction was conducted in a similar manner to that of Example 1 except that p-chlorobenzo-trichloride was replaced by m-chlorobenzotrichloride. The conversion was 34.1%. The reaction yield of intended m,p'-dichlorobenzophenone was 89%.

EXAMPLE 5

The reaction was conducted in a similar manner to that of Example 3 except that the silica/alumina catalyst was replaced by alumina treated with sulfuric acid (i.e. alumina immersed in dilute sulfuric acid and then calcined at 600° C. for 3 hours) and that the reaction time was altered to 1 hour. The results are given in Table 3.

TABLE 3

| Number of times of repetition | Conversion (%) | Rate of p,p'-compound formation (%) | Yield (%) |
|---|---|---|---|
| 1 | 44.6 | 38.2 | 85.7 |
| 2 | 43.7 | 38.1 | 87.2 |
| 3 | 43.7 | 37.5 | 85.8 |
| 4 | 42.6 | 36.4 | 85.4 |
| 5 | 41.2 | 35.8 | 86.9 |
| 6 | 42.3 | 35.7 | 84.4 |
| 7 | 43.2 | 36.7 | 85.0 |
| 8 | 43.6 | 37.9 | 86.9 |
| 9 | 42.8 | 37.1 | 86.7 |
| 10 | 40.5 | 35.8 | 88.4 |

COMPARATIVE EXAMPLE

The reaction was conducted in a similar manner to that of Example 3 except that the silica/alumina catalyst was replaced by zeolite. Since a lowering in the conversion during the repeated use of the catalyst was serious, the catalyst was repeatedly used only three times. The results are given in Table 4.

TABLE 4

| | Y-Zeolite | | Hyperstable HY-zeolite | | Mordenite H | |
|---|---|---|---|---|---|---|
| Number of times of repetition | Conversion (%) | Rate of p,p'-compound formation (%) | Conversion (%) | Rate of p,p'-compound formation (%) | Conversion (%) | Rate of p,p'-compound formation (%) |
| 1 | 48.1 | 36.8 | 64.0 | 50.6 | 24.1 | 18.8 |
| 2 | 28.8 | 27.0 | 33.0 | 28.2 | 13.8 | 12.1 |
| 3 | 27.1 | 24.9 | 26.7 | 24.5 | 12.0 | 11.4 |

We claim:

1. A process for producing a p-halogenobenzophenone derivative characterized by reacting an (un)substituted benzotrichloride of the following formula (I) with a halogenobenzene of the following formula (II) in the presence of a catalyst selected from the group consisting of alumina, nickel sulfate, zirconium oxide, amorphous silica/alumina and a mixture of two or more of them or a catalyst obtained by treating these compounds with an acid and hydrolyzing the resulting bisphenyldichloromethane of the following formula (III):

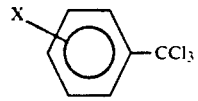 (I)

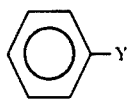 (II)

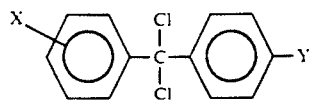 (III)

wherein X represents a halogen atom or a hydrogen atom and Y represents a halogen atom.

2. A process for producing a p-halogenobenzophenone derivative according to claim 1, wherein the catalyst treated with an acid is one treated with sulfuric or hydrofluoric acid.

3. A process for producing a p-halogenobenzophenone derivative according to claim 1, wherein the reaction is conducted at a reaction temperature ranging from 80° to 200° C.

* * * * *